United States Patent
Horiuchi et al.

(10) Patent No.: US 7,576,220 B2
(45) Date of Patent: Aug. 18, 2009

(54) METHOD OF PRODUCING 1,2,4-OXADIAZOLE DERIVATIVES

(75) Inventors: Akira Horiuchi, Tokyo (JP); Ken-ichi Itoh, Saitama (JP); Hiroshi Sakamaki, Chiba (JP)

(73) Assignee: Rikkyo Gakuin, Tokyo (JP)

( * ) Notice: Subject to any disclaimer, the term of this patent is extended or adjusted under 35 U.S.C. 154(b) by 333 days.

(21) Appl. No.: 11/662,280

(22) PCT Filed: Apr. 6, 2006

(86) PCT No.: PCT/JP2006/007351

§ 371 (c)(1),
(2), (4) Date: Mar. 9, 2007

(87) PCT Pub. No.: WO2006/123486

PCT Pub. Date: Nov. 23, 2006

(65) Prior Publication Data

US 2008/0086009 A1   Apr. 10, 2008

(30) Foreign Application Priority Data

May 16, 2005   (JP)   ............... 2005-142692

(51) Int. Cl.
*C07D 271/12*   (2006.01)
(52) U.S. Cl. .................................. 548/131
(58) Field of Classification Search .............. None
See application file for complete search history.

(56) References Cited

U.S. PATENT DOCUMENTS 4,562,186 A   12/1985   Tegeler et al.

FOREIGN PATENT DOCUMENTS

| FR | 2053742 | 4/1971 |
|---|---|---|
| JP | 61-167674 | 7/1986 |

OTHER PUBLICATIONS

Ken-ichi Itoh et al., "A novel one-pot synthesis of 3-acetyl- and 3-benzoylisoxazole derivatives using ammonium cerium nitrate (CAN)", Tetrahedron Letters, vol. 43, pp. 7035-7037, 2002.
Ken-ichi Itoh et al., "Formation of isoxazole derivatives via nitrile oxide using ammonium cerium nitrate (CAN): a novel one-pot synthesis of 3-acetyl- and 3-benzoylisoxazole derivatives", Tetrahedron, vol. 60, pp. 1671-1681, 2004.
Angel Diaz-Ortiz et al., "1,3-dipolar cycloaddition of nitriles under microwave irradiation in solvent-free conditions", Heterocycles, vol. 43, No. 5, pp. 1021-1030, 1996.
John J. Tegeler et al., "Aroylnitrile oxide cyclizations. 1. Synthesis of (3-Aroyl-1,2,4-oxadiazol-5-yl)acetic acids", Journal of Heterocyclic Chemistry, vol. 24, pp. 697-699, 1987.
Ken-ichi Itoh et al., "One-Pot Synthesis of 3-Benzoyl- and 3-Acetyl-1,2,4-Oxadiazole Derivatives Using Iron(III) Nitrate", Synthesis, vol. 12, pp. 1935-1938, May 2005.
Ken-ichi Itoh et al., "A Convenient and Efficient One-Pot Synthesis of 3-Acylisoxazoles Using Iron(III) Salts", Synthesis, vol. 20, pp. 3541-3548, Oct. 2005.
Paolo Quadrelli et al., "Cycloadditions of Nitrile Oxides to Amidoximes. A General Synthesis of 3,5-Disubstituted 1,2,4-Oxadiazole-4-oxides." Tetrahedron, vol. 53, No. 5, pp. 1787-1796, 1997.
Dezso Korbonits et al., "Synthesis of Heterocycles from Aminoamide Oximes", Heterocycles, vol. 37, No. 3, pp. 2051-2068, 1994.
Robert J. Mathvink et al., "Potent, Selective Human $\beta_3$ adrenergic Receptor Agonists Containing a Substituted Indoline-5-Sulfonamide Pharmacophore", Bioorganic & Medicinal Chemistry Letters, vol. 9, pp. 1869-1874, 1999.
S. Buscemi et al., "Fluorinated Heterocyclic Compounds. An Effective Strategy for the Synthesis of Fluorinated Z-Oximes of 3-Perfluoroalkyl-6-phenyl-2H-1,2,4-triazin- 5-ones via a Ring-Enlargement Reaction of 3-Benzoyl-5-perfluoroalkyl-1,2,4-oxadiazoles and Hydrazine", J. Org. Chem., 70(8), pp. 3288-3291, Mar. 12, 2005.
G. Ponzio et al., Dioximes. VII, Gazz. claim. ital., 53, 297-305, 1923 (abstract), Retrieved from STN International, CAPLUS Accession No. 1923:25980, Registry No. 861, 334-81-8.

*Primary Examiner*—Kamal A Saeed
(74) *Attorney, Agent, or Firm*—Wenderoth, Lind & Ponack, L.L.P.

(57) ABSTRACT

A method for producing a 1,2,4-oxadiazol derivative represented by the formula (1): (1) [wherein, $R^1$ represents a methyl group or a phenyl group, and $R^2$ represents an optionally substituted linear or branched alkyl group], which comprises reacting a nitrile represented by the formula (2): (2) [wherein, $R^2$ represents an optionally substituted linear or branched alkyl group] with acetone or acetophenone in the presence of iron (III) nitrate. The method allows a 1,2,4-oxadiazol derivative exhibiting a useful biological activity to be produced in good yield without the discharge of a harmful waste.

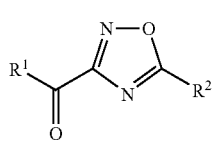

8 Claims, No Drawings

METHOD OF PRODUCING 1,2,4-OXADIAZOLE DERIVATIVES

TECHNICAL FIELD

The present invention relates to a method of producing 1,2,4-oxadiazole derivatives and more particularly relates to a novel, high-yield method of producing 1,2,4-oxadiazole derivatives that uses a nitrile and iron(III) nitrate and that does not discharge wastes.

BACKGROUND ART

Analogue compounds having the 1,2,4-oxadiazole derivative skeleton exhibit, inter alia, an antikinetoplastid activity and an anti-inflammatory action and are known as $\beta_3$ adrenergic receptor agonists, muscarinic agonists, serotonin antagonists, and non-steroidal anti-inflammatories.

1,2,4-oxadiazole derivatives have been produced by the cycloaddition of a nitrile oxide to an amidoxime; by treating an acylated amidoxime with a base such as NaH, NaOEt, or pyridine; and by acylating an amidoxime with an activated carboxylic acid derivative, for example, an ester or acid chloride, followed by cyclodehydration (see, for example, Nonpatent Documents 1, 2, and 3, infra).

A one-step method is also known for the preparation of 3-acetyl- and 3-benzoylisoxazole derivatives using ammonium cerium nitrate (CAN) (see, for example, Nonpatent Document 4, infra).

It is also known that when ammonium cerium(IV) nitrate (abbreviated below as CAN(IV)) is reacted, at 80° C. in acetophenone or under reflux in acetone, with a compound having a carbon-carbon unsaturated double or triple bond, such as an alkene or alkyne, an isoxazole derivative is obtained in high yield in a single step by a 1,3-dipolar cycloaddition that proceeds via nitration of the solvent molecule and production of the nitrile oxide, and, moreover, that the same reactions occur, with an inhibition of the production of by-products and additional improvements in the yield, using ammonium cerium(III) nitrate (abbreviated below as CAN(III)) and formic acid in place of CAN(IV) (see, for example, Nonpatent Document 5, infra).

It is also known that similar isoxazole derivatives are obtained by reaction using nontoxic iron(III) nitrate (see, for example, Nonpatent Documents 6 and 7, infra).

Nonpatent Document 1: Quardrelli, P.; Invernizzi, A. G.; Falzoni, M.; Caramella, P. Tetrahedron 1997, 53, 1787.

Nonpatent Document 2: Korbonits, D.; Horvath, K. Heterocycles 1994, 37, 2051.

Nonpatent Document 3: Mathvink, R. J.; Barrtta, A. M.; Candelore, M. R.; Cascieri, M. A.; Deng, L.; Tota, L.; Strader, C. D.; Wyvratt, M. J.; Fisher, M. H.; Weber, A. E. Bioorg. Med. Chem. Lett. 1999, 9, 1869.

Nonpatent Document 4: Itoh, K.; Takahashi, S.; Ueki, T.; Sugiyama, T.; Takahashi, T. T.; Horiuchi, C. A.; Tetrahedron Lett. 2002, 43, 7035.

Nonpatent Document 5: Itoh, K.; Horiuchi, C. A. Tetrahedron 2004, 60, 1671.

Nonpatent Document 6: Tegeler, J. T.; Diamond, C. J. J. Heterocycl. Chem. 1987, 24, 697.

Nonpatent Document 7: Diaz-Ortiz, A.; Diez-Barra, E.; Hoz, A. D. L.; Moreno, A.; Gomez-Escalonilla, M. J.; Loupy, A. Heterocycles 1996, 43, 1021.

DISCLOSURE OF THE INVENTION

Problems to Be Solved by the Invention

The methods described in Nonpatent Documents 1, 2, and 3 are complicated and uneconomical because they require a plurality of steps; moreover, the target compound yields are not good.

The synthesis methods using CAN(IV) and CAN(III) as described in Nonpatent Documents 4 and 5 are also associated with several problems: they discharge toxic cerium-containing wastes, which raises the issue of environmental pollution, and therefore entail high costs for waste treatment; moreover, their yields are not always satisfactory.

An object of the present invention, therefore, is to provide a novel, high-yield method of producing 1,2,4-oxadiazole derivatives that does not discharge wastes, that uses a nitrile as a starting compound, and that employs iron(III) nitrate.

Means Solving the Problems

The present inventors carried out extensive and intensive investigations in order to achieve the aforementioned object. As a consequence, the present inventors carried out research into whether it would possible to obtain 1,2,4-oxadiazole derivatives using nontoxic iron(III) nitrate. It was discovered as a result that 3-acetyl-1,2,4-oxadiazole derivatives and 3-benzoyl-1,2,4-oxadiazole derivatives can be prepared in a single step using a nitrile rather than an alkyne as a starting substrate.

As a novel, high-yield method of producing 1,2,4-oxadiazole derivatives that does not discharge wastes, that uses a nitrile as a starting compound, and that employs iron(III) nitrate, the present invention has the following characteristic features in order to solve the problems identified above.

(1) A 1,2,4-oxadiazole derivative represented by formula (1)

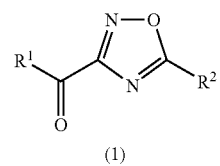

wherein $R^1$ represents a methyl group or a phenyl group and $R^2$ represents a possibly substituted, straight-chain or branched alkyl group.

(2) The 1,2,4-oxadiazole derivative according to (1), wherein the 1,2,4-oxadiazole derivative is a 3-acetyl-1,2,4-oxadiazole derivative or a 3-benzoyl-1,2,4-oxadiazole derivative.

(3) The 1,2,4-oxadiazole derivative according to (1) or (2), wherein the 1,2,4-oxadiazole derivative is 3-acetyl-5-methyl-1,2,4-oxadiazole, 3-acetyl-5-ethyl-1,2,4-oxadiazole, 3-acetyl-5-propyl-1,2,4-oxadiazole, 3-acetyl-5-isopropyl-1,2,4-oxadiazole, 3-benzoyl-5-methyl-1,2,4-oxadiazole, 3-benzoyl-5-ethyl-1,2,4-oxadiazole, 3-benzoyl-5-propyl-1,2,4-oxadiazole, or 3-benzoyl-5-isopropyl-1,2,4-oxadiazole.

(4) A method of producing a 1,2,4-oxadiazole derivative represented by formula (1)

[C3]

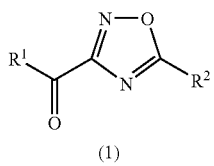

(1)

(wherein $R^1$ represents methyl or phenyl and $R^2$ represents a possibly substituted, straight-chain or branched alkyl group) wherein a nitrile with formula (2)

[C2]

$$R^2C\equiv N \qquad (2)$$

(wherein $R^2$ represents a possibly substituted, straight-chain or branched alkyl group) is reacted with acetone or acetophenone in the presence of iron(III) nitrate.

(5) The method according to (4) of producing a 1,2,4-oxadiazole derivative, wherein the nitrile is acetonitrile, propionitrile, or butyronitrile.

(6) The method according to (4) or (5) of producing a 1,2,4-oxadiazole derivative, characterized in that the 1,2,4-oxadiazole derivative is a 3-acetyl-1,2,4-oxadiazole derivative or a 3-benzoyl-1,2,4-oxadiazole derivative.

(7) The method according to any of (4) to (6) of producing a 1,2,4-oxadiazole derivative, wherein the 1,2,4-oxadiazole derivative is 3-acetyl-5-methyl-1,2,4-oxadiazole, 3-acetyl-5-ethyl-1,2,4-oxadiazole, 3-acetyl-5-propyl-1,2,4-oxadiazole, 3-acetyl-5-isopropyl-1,2,4-oxadiazole, 3-benzoyl-5-methyl-1,2,4-oxadiazole, 3-benzoyl-5-ethyl-1,2,4-oxadiazole, 3-benzoyl-5-propyl-1,2,4-oxadiazole, or 3-benzoyl-5-isopropyl-1,2,4-oxadiazole.

BEST MODE FOR CARRYING OUT THE INVENTION

The 1,2,4-oxadiazole derivatives according to the present invention and the individual constituent requisites of their method of production are described in detail in the following.

The 1,2,4-oxadiazole derivatives according to the present invention are represented by formula (1).

$R^1$ in formula (1) represents methyl or phenyl. $R^2$ represents a possibly substituted, straight-chain or-branched alkyl group.

Possibly substituted, straight-chain or branched alkyl $R^2$ that can be used in the present invention is preferably $C_{1-12}$ alkyl and particularly preferably is $C_{1-9}$ alkyl.

Specific examples of the alkyl group are methyl, trifluoromethyl, trichloromethyl, dichloromethyl, iodomethyl, bromomethyl, ethyl, 2,2,2-trifluoroethyl, 2,2,2-trichloroethyl, pentafluoroethyl, n-propyl, isopropyl, n-butyl, isobutyl, sec-butyl, t-butyl, n-pentyl, isoamyl, n-hexyl, n-heptyl, 1-methylhexyl, 3-methylhexyl, 4-methylhexyl, 5-methylhexyl, 1-ethylpentyl, 1,1-diethylpentyl, 1,4-diethylpentyl, 1,1-diethylpropyl, 1,3,3-trimethylbutyl, 1-ethyl-2,2-dimethylpropyl, n-octyl, 1-methylheptyl, 1-ethylhexyl, 2-ethylhexyl, 1-propylpentyl, 1,1-dimethylhexyl, 1-ethyl-1-methylpentyl, 2,4,4-trimethylpentyl, 1,1,3,3-tetramethylbutyl, n-nonyl, 1-methyloctyl, 1-ethylheptyl, 1,5,5-trimethylhexyl, n-decyl, 1-methylnonyl, 1,1-dimethyloctyl, 3,7-dimethyloctyl, n-undecanyl, 1-methyldecyl, and n-dodecyl, The substituent can be exemplified by halogen atoms such as fluorine, chlorine, bromine, and iodine; the nitro group; the cyano group; alkyl such as possibly substituted methyl, ethyl, propyl, butyl, isobutyl, sec-butyl, t-butyl, and pentyl; cycloalkyl such as possibly substituted cyclobutyl, cyclopentyl, and cyclohexyl; possibly substituted methylthio; possibly substituted phenyl; naphthyl such as 1-naphthyl and 2-naphthyl; nonaromatic heterocyclic groups such as possibly substituted 1-pyrrolidyl, piperidine, and morpholino; aromatic heterocyclic groups such as possibly substituted 2-furyl, 3-furyl, 2-thienyl, 2-pyridyl, 1-pyrrolyl, 1-imidazoyl, and 1-pyrazolyl; alkoxyl such as possibly substituted methoxy, ethoxy, propoxy, butoxy, hexyloxy, and nonyloxy; a possibly substituted carboxyl group; a possibly substituted alkoxycarbonyl group; an acyl group such as possibly substituted acetyl, propionyl, butyryl, and benzoyl; an amino group such as possibly substituted methylamino, ethylamino, diethylamino, acetylamino, benzoylamino, and phenylamino; an hydroxyl group such as possibly substituted methoxy, ethoxy, propoxy, butoxy, isobutoxy, sec-butoxy, t-butoxy, and hexyloxy; a thiol group such as ethylthio, cyclobutylthio, phenylthio, and 2-pyridinethio; carbonyl; and possibly esterified or amidized carboxyl such as ethoxycarbonyl.

In accordance with the production method according to the present invention, a nitrile with formula (2) is reacted with acetone or acetophenone in the presence of iron(III) nitrate.

$R^2$ in formula (2) represents a possibly substituted, straight-chain or branched alkyl group. The possibly substituted, straight-chain or branched alkyl $R^2$ is preferably $C_{1-12}$ alkyl and particularly preferably is $C_{1-9}$ alkyl. This alkyl can be specifically exemplified by the groups already cited above, and the substituents are also the same as the substituents already cited above.

The reaction temperature that can be used in the present invention can be selected as appropriate in view, for example, of the type of nitrile and is preferably 50 to 150° C. and particularly preferably is approximately 56 to 80° C. In general, when acetone is used as the ketone, the reaction is preferably carried out under an acetone reflux, while when acetophenone is used, the reaction is preferably run at 80° C. The ability to obtain the target 1,2,4-oxadiazole derivative in high yields is impaired when the reaction temperature falls below the aforementioned temperature range or exceeds the aforementioned temperature range.

With regard to the pressure used in this reaction, the reaction can be run at ambient pressure or under any known overpressure.

The reaction time usable in the present invention is set in correspondence to the reaction temperature and pressure, but, for example, about 10 to 30 hours is preferred and 18 to 22 hours is more preferred. Reaction times below 10 hours and above 30 hours are undesirable because the yield deteriorates at such reaction times.

The nitrile employed in the present invention is used preferably at 10.0 to 50.0 mol equiv. per 1.0 mol equiv. iron(III) nitrate. The yield undesirably deteriorates outside this use quantity range of 10.0 to 50.0 mol equiv.

The ketone is used preferably at 2.5 to 10.0 mol equiv. per 1.0 mol equiv. iron(III) nitrate. The yield undesirably deteriorates outside this use quantity range of 2.5 to 10.0 mol equiv.

The ketones usable in the reaction of the present invention are acetone and acetophenone, and the use of acetophenone provides higher yields of the target 1,2,4-oxadiazole derivative than does the use of acetone.

EXAMPLES

Embodiments of the present invention are described in additional detail by the examples given below, but the present invention is not limited to the scope described by these examples, insofar as the gist of the present invention is not exceeded.

The nitriles, iron(III) nitrate, ammonium cerium(IV) nitrate, sodium nitrate, magnesium nitrate, ammonium nitrate, acetone, and acetophenone used in the examples of the present invention were all obtained from commercial sources.

The following measurement instrumentation was used to identify the structure and measure the properties of the 1,2,4-oxadiazole derivatives that were products according to the present invention.

IR: FT-IR-230 spectrometer (JASCO Corporation)
$^1$H and $^{13}$C-NMR: JEOL GSX400 (JEOL Ltd.)
GC: Shimadzu Gas Chromatogram GC-14A (Shimadzu)
GC-MS: GCMS-QP5050 (Shimadzu)
HRMS: JEOL JMS-O1SG-2
GCL: HP5890 (Hewlett-Packard)

Examples 1 to 14

<Investigation of the Conditions in the Reaction of Iron(III) Nitrate with Acetonitrile (1) and Acetophenone>

3-benzoyl-5-methyl-1,2,4-oxadiazole (1a) was obtained by the reaction of acetonitrile (1) and acetophenone with iron(III) nitrate at 80° C. according to the reaction scheme shown below. The IR spectrum of compound (1a) exhibited absorptions at 1713, 1681, and 1581 cm$^{-1}$. An absorption at $\delta$=2.71 (3H, CH$_3$) was present in the $^1$H-NMR spectrum. The $^{13}$C-NMR presented the known signals at $\delta$=182.5, 177.3, and 165.4 based on the carbonyl carbon and the respective carbons in the 1,2,4-oxadiazole ring. Compound 1a was therefore confirmed to be 3-benzoyl-5-methyl-1,2,4-oxadiazole.

The reaction conditions are shown in Table 1 below.

As shown in Examples 1 to 5 shown in the following Table 1, acetonitrile (1) was used as the solvent in this reaction. The reason for this is the low reactivity of acetonitrile (1) in the 1,3-dipolar cycloaddition. In addition, the product yields are based on the amount of iron(III) nitrate used because the reaction requires excess ketone and nitrile with reference to the iron(III) nitrate.

As shown by Example 9 shown in Table 1 below, the corresponding 1,2,4-oxadiazole derivative 1a was obtained at a high yield of 95% when acetophenone (5.0 mmol), acetonitrile (1; 4.5 mL), and iron(III) nitrate (1.0 mmol) were used.

Reaction scheme

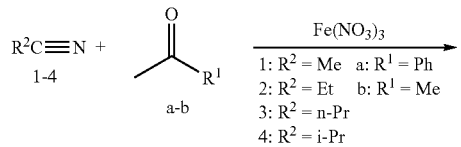

[C4]

1: R$^2$ = Me   a: R$^1$ = Ph
2: R$^2$ = Et   b: R$^1$ = Me
3: R$^2$ = n-Pr
4: R$^2$ = i-Pr

-continued

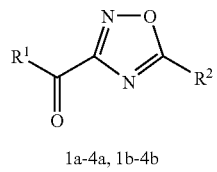

1a-4a, 1b-4b

The labels in the preceding reaction scheme refer to the following groups.

Me: methyl, i.e., R$^2$=Me: acetonitrile (nitrile 1)
Et: ethyl, i.e., R$^2$=Et: propionitrile (nitrile 2)
n-Pr: normal-propyl, i.e., R$^2$=n-Pr: butyronitrile (nitrile 3)
i-Pr: isopropyl, i.e., R$^2$=i-Pr: isobutyronitrile (nitrile 4)
Ph: phenyl

TABLE 1

| | Reaction conditions | | | | |
|---|---|---|---|---|---|
| example[a] | acetophenone (mmol) | acetonitrile (1) (mmol) | Fe(NO$_3$)$_3$ (mmol) | time (h) | product, yield (%)[b] |
| 1 | 4.5 mL | 1.0 | 1.0 | 20 | 1a (trace) |
| 2 | 4.5 mL | 10.0 | 1.0 | 20 | 1a (16) |
| 3 | 4.5 mL | 20.0 | 1.0 | 18 | 1a (27) |
| 4 | 4.5 mL | 40.0 | 1.0 | 18 | 1a (55) |
| 5 | 4.5 mL | 50.0 | 1.0 | 18 | 1a (49) |
| 6 | 1.0 | 4.5 mL | 1.0 | 22 | 1a (4) |
| 7 | 2.0 | 4.5 mL | 1.0 | 20 | 1a (27) |
| 8 | 4.0 | 4.5 mL | 1.0 | 18 | 1a (72) |
| 9 | 5.0 | 4.5 mL | 1.0 | 18 | 1a (95) |
| 10 | 5.0 | 4.5 mL | 2.0 | 20 | 1a (69) |
| 11 | 5.0 | 4.5 mL | 3.0 | 22 | 1a (48) |
| 12 | 5.0 | 4.5 mL | 4.0 | 22 | 1a (25) |
| 13 | 7.5 | 4.5 mL | 1.0 | 18 | 1a (94) |
| 14 | 10.0 | 4.5 mL | 1.0 | 18 | 1a (80) |

[a]Reaction conditions: acetophenone, acetonitrile (1), and iron(III) nitrate were reacted at 80° C.
[b]The yield was determined based on the amount of iron(III) nitrate used, by GLC analysis using n-dodecane as internal hydrocarbon standard.

Examples 15 to 24

<Reaction of Ketones and Various Nitriles Using Iron(III) Nitrate>

Based on the aforementioned investigation of reaction conditions, reactions were carried out as shown in Examples 15 to 17 shown in of Table 2 below using the nitrites 2 to 4 cited in the preceding reaction scheme. The corresponding 3-benzoyl-1,2,4-oxadiazole derivatives 2a to 4a were obtained in yields of 44 to 95% as a result.

3-acetyl-5-methyl-1,2,4-oxadiazole (1b) was obtained from the reaction using acetone, as shown in Examples 18 to 21 in Table 2 below. The IR spectrum of compound 1b exhibited absorptions at 1731, 1699, and 1601 cm$^{-1}$. An absorption at $\delta$=2.70 (3H, CH$_3$) was present in the $^1$H-NMR spectrum. The $^{13}$C-NMR spectrum presented the known signals at $\delta$=188.8, 178.5, and 165.8 ppm based on the carbonyl carbon and the respective carbons in the 1,2,4-oxadiazole ring.

As shown in Example 19 shown in Table 2 below, the corresponding 1,2,4-oxadiazole derivative 1b was obtained in a yield of 61% by the reaction of acetone (5.0 mmol) and acetonitrile (1; 4.5 mL) with iron(III) nitrate (1.0 mmol) under reflux.

As shown in Examples 22 to 24 shown in Table 2 below, 3-acetyl-1,2,4-oxadiazoles 2b to 4b were similarly obtained from nitrites 2 to 4 in yields of 25 to 62% under these reaction conditions.

Based on these results, it can be concluded that the production of the 3-benzoyl-1,2,4-oxadiazole derivatives 1a to 4a from acetophenone and various nitrites proceeds more smoothly than the production of the 3-acetyl-1,2,4-oxadiazole derivatives 1b to 4b.

TABLE 2

Reaction of ketones and various nitriles using iron(III) nitrate

| example[a] | nitrile | ketone | mol equiv. | time (h) | product, yield (%)[b] |
|---|---|---|---|---|---|
| 15 | 2 | acetophenone | 5.0 | 20 | 2a (95) |
| 16 | 3 | acetophenone | 5.0 | 20 | 3a (95) |
| 17 | 4 | acetophenone | 5.0 | 22 | 4a (44) |
| 18 | 1 | acetone | 2.5 | 18 | 1b (47) |
| 19 | 1 | acetone | 5.0 | 16 | 1b (61) |
| 20 | 1 | acetone | 7.5 | 16 | 1b (50) |
| 21 | 1 | acetone | 10.0 | 14 | 1b (44) |
| 22 | 2 | acetone | 5.0 | 16 | 2b (62) |
| 23 | 3 | acetone | 5.0 | 16 | 3b (61) |
| 24 | 4 | acetone | 5.0 | 18 | 4b (25) |

[a]Reaction conditions: acetophenone (5.0 mmol), nitrile 2-4 (4.5 ml), and iron(III) nitrate $Fe(NO_3)_3$ (1.0 mmol) were reacted at 80° C. Acetone (2.5 to 10.0 mmol), nitrile 1-4 (4.5 ml), and $Fe(NO_3)_3$ (1.0 mmol) were reacted under reflux.
[b]The yield was determined based on the amount metal nitrates used, by GLC analysis using n-dodecane as internal hydrocarbon standard.

Examples 25 to 28

<Use of Various Metal Nitrates in the Reaction of Acetophenone and Acetonitrile>

In order to examine the reaction mechanism, various metal nitrates were reacted with acetophenone and acetonitrile (1) as shown in Table 3 below.

As shown by Example 25 in Table 3 below, the corresponding 1,2,4-oxadiazole derivative 1a was obtained in a yield of 78% using CAN(IV); however, the use of CAN(IV) is undesirable from the standpoint of environmental pollution due to the associated production of wastes containing toxic cerium metal.

However, the reaction did not occur with the use of $NaNO_3$, $Mg(NO_3)_2$, or $NH_4NO_3$, as shown in Examples 26 to 28 in Table 3 below.

The present inventors have recently reported that CAN(IV) accelerates the enolization of ketones. The reaction mechanism given below has been proposed based on this report. According to this reaction mechanism, enolization of the ketone is accelerated by $Fe(NO_3)_3$ or CAN(IV), after which the ketone undergoes nitration. The nitrile oxide is formed by the acid-catalyzed dehydration of the α-nitroketone, and the 3-benzoyl- or 3-acetyl-1,2,4-oxadiazole derivative is then obtained by 1,3-dipolar cycloaddition. The product yield therefore depends on the stability of the nitrite oxide and the reactivity of the nitrite in 1,3-dipolar cycloaddition.

Thus, the method of the present invention, which uses nontoxic and inexpensive iron(III) nitrate, is a simple and high yield method for producing 3-benzoyl- and 3-acetyl-1,2,4-oxadiazole derivatives that also does not produce toxic wastes.

Reaction mechanism

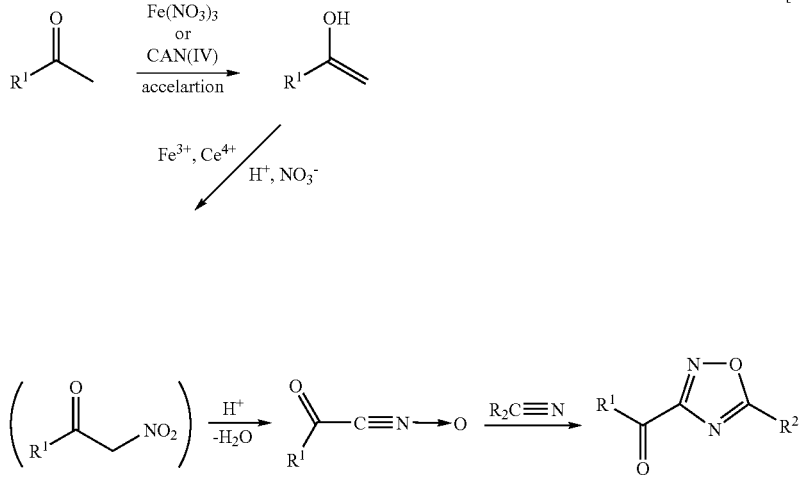

[C4]

TABLE 3

Use of various metal nitrates

| example[a] | metal nitrate | time (h) | product (%)[b] |
|---|---|---|---|
| 25 | CAN(IV) | 18 | 1a (78) |
| 26 | NaNO$_3$ | 30 | no reaction |
| 27 | Mg(NO$_3$)$_2$ | 30 | no reaction |
| 28 | NH$_4$NO$_3$ | 30 | no reaction |

[a]Reaction conditions: acetophenone (5.0 mmol), acetonitrile (1; 4.5 mL), and the metal nitrate (1.0 mmol) were reacted at 80° C.
[b]The yield was determined based on the amount of iron(III) nitrate used, by GLC analysis using n-dodecane as internal hydrocarbon standard.

Production methods using the present invention and spectroscopic data for the obtained products 1a to 4a and products 1b to 4b are given below.

<Production Method 1>

<Reaction of Acetonitrile (1) and Acetophenone with Iron (III) Nitrate>

A mixture of acetonitrile (1; 4.5 mL), acetophenone (0.6008 g, 5.0 mmol), and iron(III) nitrate (0.4040 g, 1.0 mmol) was reacted at 80° C. for 18 hours while stirring. After completion of the reaction, the liquid reaction mixture was filtered and the liquid reaction mixture was extracted with ethyl acetate (50 mL). This was followed by washing with saturated aqueous sodium bicarbonate solution (2×2.0 mL), saturated aqueous sodium chloride solution (2×2.0 mL), and distilled water (2×2.0 mL) in the sequence given. The solution was then dried over anhydrous sodium sulfate; the residual acetophenone was removed by distillation in vacuo; and concentration was carried out under reduced pressure. The resulting light yellow oil was subjected to silica gel chromatography. Separation by hexane-ethyl acetate (4:1) gave 3-benzoyl-5-methyl-1,2,4-oxadiazole (1a) as a light yellow oil (0.1504 g).

<Spectroscopic data 1>

3-benzoyl-5-methyl-1,2,4-oxadiazole (1a): light yellow oil.

IR (NaCl): 1713, 1681, 1581 cm$^{-1}$.

$^1$H-NMR (CDCl$_3$): δ=8.25-8.27 (m, 2H), 7.50-7.68 (m, 3H), 2.71 (s, 3H).

$^{13}$C-NMR (CDCl$_3$): δ=182.5, 177.3, 165.4, 134.7, 134.3, 130.3, 128.4, 12.0.

HRMS: m/z [M] calculated for C$_{10}$H$_8$N$_2$O$_2$: 188.0586; found [M]$^+$: 188.0583.

3-benzoyl-5-ethyl-1,2,4-oxadiazole (2a): light yellow oil.

IR (NaCl): 1711, 1679, 1577 cm$^{-1}$.

$^1$H-NMR (CDCl$_3$): δ=8.25-8.30 (m, 2H), 7.46-7.61 (m, 3H), 3.06 (q, J=7.68 Hz, 2H), 1.49 (t, J=7.68 Hz, 3H).

$^{13}$C-NMR (CDCl$_3$): δ=183.0, 165.6, 154.3, 135.3, 134.6, 130.6, 128.7, 20.3, 10.7.

HRMS: m/z [M] calculated for C$_{11}$H$_{10}$N$_2$O$_2$: 202.0742; found [M]$^+$: 202.0749.

3-benzoyl-5-propyl-1,2,4-oxadiazole (3a): light yellow oil.

IR (NaCl): 1712, 1679, 1580 cm$^{-1}$.

$^1$H-NMR (CDCl$_3$): δ=8.28-8.33 (m, 2H), 7.46-7.62 (m, 3H), 3.01 (t, J=7.56 Hz, 2H), 1.90-1.99 (m, 2H), 1.07 (t, J=7.56 Hz, 3H).

$^{13}$C-NMR (CDCl$_3$): δ=183.0, 171.3, 165.6, 135.1, 134.6, 130.6, 128.7, 28.4, 20.1, 13.6.

HRMS: m/z [M] calculated for C$_{12}$H$_{12}$N$_2$O$_2$: 216.0899; found [M]$^+$: 216.0898.

3-benzoyl-5-isopropyl-1,2,4-oxadiazole (4a): light yellow oil. IR (NaCl): 1711, 1677, 1569 cm$^{-1}$.

$^1$H-NMR (CDCl$_3$): δ=8.27-8.30 (m, 2H), 7.46-7.61 (m, 3H), 3.34-3.41 (m, 1H), 1.50 (d, J=6.83 Hz, 6H).

$^{13}$C-NMR (CDCl$_3$): δ=183.1, 171.1, 165.5, 135.2, 134.5, 130.6, 128.7, 27.6, 20.1.

HRMS: m/z [M] calculated for C$_{12}$H$_{12}$N$_2$O$_2$: 216.0899; found [M]$^+$: 216.0892.

<Production Method 2>

<Reaction of Acetonitrile (1) and Acetone with Iron(III) Nitrate>

A mixture of acetonitrile (1; 4.5 mL), acetone (0.2904 g, 5.0 mmol), and iron(III) nitrate (0.4040 g, 1.0 mmol) was reacted under reflux for 16 hours while stirring. After completion of the reaction, the liquid reaction mixture was filtered and the liquid reaction mixture was extracted with ethyl acetate (50 mL). This was followed by washing with saturated aqueous sodium bicarbonate solution (2×2.0 mL), saturated aqueous sodium chloride solution (2×2.0 mL), and distilled water (2×2.0 mL) in the sequence given. The solution was then dried over anhydrous sodium sulfate; the residual acetone was removed by distillation in vacuo; and concentration was carried out under reduced pressure. The resulting light yellow oil was subjected to silica gel chromatography. Separation by hexane-ethyl acetate (4:1) gave 3-acetyl-5-methyl-1,2,4-oxadiazole (1b) as a light yellow oil (0.0504 g).

<Spectroscopic Data 2>

3-acetyl-5-methyl-1,2,4-oxadiazole (1b): light yellow oil.

IR (NaCl): 1731, 1699, 1601 cm$^{-1}$.

$^1$H-NMR (CDCl$_3$) : δ=2.70 (s, 6H).

$^{13}$C-NMR (CDCl$_3$): δ=188.8, 178.5, 165.8, 27.8, 12.4.

HRMS: m/z [M] calculated for C$_5$H$_6$N$_2$O$_2$: 126.0429; found [M]$^+$: 126.0433.

3-acetyl-5-ethyl-1,2,4-oxadiazole (2b): light yellow oil.

IR (NaCl): 1738, 1688, 1599 cm$^{-1}$.

$^1$H-NMR (CDCl$_3$): δ=3.02 (q, J=7.56 Hz, 2H), 2.70 (s, 3H), 1.45 (t, J=7.56 Hz, 3H).

$^{13}$C-NMR (CDCl$_3$): δ=189.1, 182.7, 165.7, 27.8, 20.3, 10.6.

HRMS: m/z [M] calculated for C$_6$H$_8$N$_2$O$_2$: 140.0586; found [M]$^+$: 140.0587.

3-acetyl-5-propyl-1,2,4-oxadiazole (3b): light yellow oil.

IR (NaCl): 1733, 1691, 1589 cm$^{-1}$.

$^1$H-NMR (CDCl$_3$): δ=2.96 (t, J=7.44 Hz, 2H), 2.70 (s, 3H), 1.86-1.95 (m, 2H), 1.04 (t, J=7.44 Hz, 3H).

$^{13}$C-NMR (CDCl$_3$): δ=189.0, 181.7, 165.8, 28.4, 27.9, 20.1, 13.6.

HRMS: m/z [M] calculated for C$_7$H$_{10}$N$_2$O$_2$: 154.0742: found [M]$^+$: 154.0733.

3-acetyl-5-isopropyl-1,2,4-oxadiazole (4b): light yellow oil.

IR (NaCl): 1732, 1694, 1593 cm$^{-1}$.

$^1$H-NMR (CDCl$_3$): δ=3.28-3.35 (m, 1H), 2.70 (s, 3H), 1.45 (d, J=6.83 Hz, 6H).

$^{13}$C-NMR (CDCl$_3$): δ=189.1, 185.7, 165.8, 27.9, 27.6, 20.1.

HRMS: m/z [M] calculated for C$_7$H$_{10}$N$_2$O$_2$: 154.0742; found [M]$^+$: 154.0733.

INDUSTRIAL APPLICABILITY

The 1,2,4-oxadiazole derivatives according to the present invention can be expected to have a pharmacological action as a β$_3$ adrenergic receptor agonist, muscarinic agonist, seratonin antagonist, and non-steroidal anti-inflammatory.

The iron(III) nitrate used in the production method is inexpensive, contains an environmentally accommodative metal, and is an excellent reagent that is easy to manage, and as a consequence 1,2,4-oxadiazole derivatives can be obtained by an environmentally friendly method.

In addition, the 1,2,4-oxadiazole ring can be synthesized in a single step. Moreover, the use of acetophenone provides the target compounds in higher yields than does the use of acetone, and the target compounds can be obtained in high yields without a waste treatment process.

The invention claimed is:

1. A method of producing a 1,2,4-oxadiazole derivative represented by formula (1)

[C7]

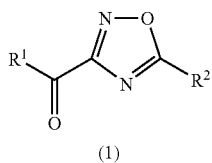

(1)

(wherein R$^1$ represents a methyl group or a phenyl group and R$^2$ represents a possibly substituted, straight-chain or branched alkyl group), characterized by reacting a nitrile represented by formula (2)

[C6]

(wherein R$^2$ represents a possibly substituted, straight-chain or branched alkyl group) with acetone or acetophenone in the presence of iron(III) nitrate.

2. The method of producing a 1,2,4-oxadiazole derivative according to claim 1,
wherein the nitrile is acetonitrile, propionitrile, or butyronitrile.

3. The method of producing a 1,2,4-oxadiazole derivative according to claim 1,
wherein the 1,2,4-oxadiazole derivative is a 3-acetyl-1,2,4-oxadiazole derivative or a 3-benzoyl-1,2,4-oxadiazole derivative.

4. The method of producing a 1,2,4-oxadiazole derivative according claim 1,
wherein the 1,2,4-oxadiazole derivative is 3-acetyl-5-methyl-1,2,4-oxadiazole, 3-acetyl-5-ethyl-1,2,4-oxadiazole, 3-acetyl-5-propyl-1,2,4-oxadiazole, 3-acetyl-5-isopropyl-1,2,4-oxadiazole, 3-benzoyl-5-methyl-1,2,4-oxadiazole, 3-benzoyl-5-ethyl -1,2,4-oxadiazole, 3-benzoyl-5-propyl-1,2,4-oxadiazole, or 3 -benzoyl-5-isopropyl-1,2,4-oxadiazole.

5. The method of producing a 1,2,4-oxadiazole derivative according to claim 2,
wherein the 1,2,4-oxadiazole derivative is a 3-acetyl-1,2,4-oxadiazole derivative or a 3-benzoyl-1,2,4-oxadiazole derivative.

6. The method of producing a 1,2,4-oxadiazole derivative according to claim 2,
wherein the 1,2,4-oxadiazole derivative is 3-acetyl-5-methyl-1,2,4-oxadiazole, 3-acetyl-5-ethyl-1,2,4-oxadiazole, 3-acetyl-5-propyl-1,2,4-oxadiazole, 3-acetyl-5-isopropyl-1,2,4-oxadiazole, 3-benzoyl-5-methyl-1,2,4-oxadiazole, 3-benzoyl-5-ethyl-1,2,4-oxadiazole, 3-benzoyl-5-propyl-1,2,4-oxadiazole, or 3-benzoyl-5-isopropyl-1,2,4-oxadiazole.

7. The method of producing a 1,2,4-oxadiazole derivative according to claim 3,
wherein the 1,2,4-oxadiazole derivative is 3-acetyl-5-methyl-1,2,4-oxadiazole, 3-acetyl-5-ethyl-1,2,4-oxadiazole, 3-acetyl-5-propyl-1,2,4-oxadiazole, 3-acetyl-5-isopropyl-1,2,4-oxadiazole, 3-benzoyl-5-methyl-1,2,4-oxadiazole, 3-benzoyl-5-ethyl-1,2,4-oxadiazole, 3-benzoyl-5-propyl- 1,2,4-oxadiazole, or 3-benzoyl-5-isopropyl-1,2,4-oxadiazole.

8. The method of producing a 1,2,4-oxadiazole derivative according to claim 5,
wherein the 1,2,4-oxadiazole derivative is 3-acetyl-5-methyl-1,2,4-oxadiazole, 3-acetyl-5-ethyl-1,2,4-oxadiazole, 3-acetyl-5-propyl-1,2,4-oxadiazole, 3-acetyl-5-isopropyl-1,2,4-oxadiazole, 3-benzoyl-5-methyl-1,2,4-oxadiazole, 3-benzoyl-5-ethyl-1,2,4-oxadiazole, 3-benzoyl-5-propyl-1,2,4-oxadiazole, or 3-benzoyl-5-isopropyl-1,2,4-oxadiazole.

* * * * *